US005488954A

United States Patent [19]

Sleva et al.

[11] Patent Number: 5,488,954

[45] Date of Patent: Feb. 6, 1996

[54] ULTRASONIC TRANSDUCER AND METHOD FOR USING SAME

[75] Inventors: Michael Z. Sleva, Atlanta; William D. Hunt, Decatur; David M. Connuck, Augusta; Ronald D. Briggs, Duluth, all of Ga.

[73] Assignees: Georgia Tech Research Corp., Atlanta; Medical College of Georgia Research Institute, Augusta, both of Ga.

[21] Appl. No.: 303,638

[22] Filed: Sep. 9, 1994

[51] Int. Cl.$^6$ .............................. A61B 8/00; H01L 41/08

[52] U.S. Cl. ................ 128/662.03; 310/334; 128/662.06

[58] Field of Search ........................ 128/662.03, 662.06; 310/334, 336, 338, 339, 380

[56] References Cited

U.S. PATENT DOCUMENTS

| | | | |
|---|---|---|---|
| 5,041,849 | 8/1991 | Quate et al. | 346/140 R |
| 5,070,882 | 12/1991 | Bui et al. | 128/662.06 |
| 5,075,652 | 12/1991 | Sugai | 333/193 |
| 5,115,814 | 5/1992 | Griffith et al. | 128/662.06 |
| 5,160,870 | 11/1992 | Carson et al. | 310/339 |
| 5,207,103 | 5/1993 | Wise et al. | 128/675 X |
| 5,207,672 | 5/1993 | Roth et al. | 606/10 |
| 5,278,028 | 1/1994 | Hadimioglu et al. | 430/321 |
| 5,287,331 | 2/1994 | Schindel et al. | 367/140 |
| 5,291,090 | 3/1994 | Dias | 128/662.03 X |
| 5,368,037 | 11/1994 | Eberle et al. | 128/662.06 |
| 5,381,386 | 1/1995 | Lum et al. | 367/163 |
| 5,406,163 | 4/1995 | Carson et al. | 310/334 |

OTHER PUBLICATIONS

Integrated Silicon–PVF$_2$ Acoustic Transducer Arrays; IEEE Transactions on Electron Devices, vol. ED–26, No. 12, Dec. 1979, pp. 1921–1931; Authors: Schwartz, et al.

AP (VDF–TrFE)–based Integrated Ultrasonic Transducer; Sensors and Actuators, A21–A23 (1990) 719–725 Authors: Fiorillo, et al.

Micromachining for Improvement of Integrated Ultrasonic Transducer Sensitivity; IEEE Transactions on Electron Devices, vol. 37, No. 1, Jan. 1990, pp. 134–140 Authors: Jian–Hua Mo, et al.

Planar–Structure Focusing Lens for Operation at 200 Mhz and Its Application to the Reflection–Mode Acoustic Microscope; 1986 IEEE (1986 Ultrasonics Symposium, 745–748); Authors: Yamada, et al.

Acoustic Frasnel zone plate transducers; Applied Physics Letters, vol. 25, No. 12, Dec. 15, 1974, pp. 681–682 Authors: Farnow, et al.

Design and Construction of a PVDF Fresnel Lens; 1990 Ultrasonics Symposium, pp. 821–826 (IEEE 1990) Authors: Sleva, M. Z. and W. D. Hunt.

Ultrasound Backscatter Microscopy; Sherar, et al.; 1988 Ultrasonics Symposium, pp. 959–965 (1990 IEEE).

Integrated Piezoeletric Polymers for Microsensing and Microactuation Applications; Rashidian, et al.; DSC–vol. 32, Micromechanical Sensors, Actuators, and Systems; ASME 1991; pp. 171–179.

A High Frequency Intravascular Ultrasound Imaging System for Investigation of Vessell Wall Properties; Ryan, et al.; 1992 Ultrasonics Symposium (1992 IEEE); pp. 1101–1105.

*Primary Examiner*—Francis Jaworski
*Attorney, Agent, or Firm*—Hopkins & Thomas

[57] ABSTRACT

An improved ultrasonic transducer fabricated on a silicon base has a piezoelectric layer of polyvinylidene fluoride-trfluroethylene copolymer. The piezoelectric layer is sandwiched between two conductive electrodes, all of which are supported on a dielectric layer on top of the silicon base. At least one of the electrodes forms a Fresnel zone plate to focus the ultrasonic signals from the transducers. To improve the performance of the transducer, the silicon base behind the active area is removed, leaving the dielectric layer as a membrane to support the electrodes and the piezoelectric layer. The resulting void in the silicon base is filled with an acoustically matched backing, such as an epoxy, to enhance the wideband performance of the transducer. The transducer is especially suited for characterizing anatomical structures or features requiring very high resolution.

11 Claims, 3 Drawing Sheets

ULTRASONIC TRANSDUCER AND METHOD FOR USING SAME

FIELD OF THE INVENTION

This invention relates generally to a new and improved ultrasonic transducer. Particularly, the present invention is directed to devices and methods for generating and processing wideband ultrasonic signals for characterizing tissue, e.g., cardiovascular defects such as spatial disorder of the pulmonary medial layer, aneurysms or atherosclerotic plaque.

BACKGROUND OF THE INVENTION

Ultrasonic imaging is rapidly becoming the diagnostic modality of choice for characterizing internalized structures. In particular, miniaturized transducers mounted on probes and catheters for diagnosing and characterizing internalized structures in vivo that are accessible via endovascular or laproscopic means are know in the art, e.g., the probe tip transducers disclosed in U.S. Pat. No. 5,070,882 of Bui, et al.

In Ryan et al., "A High Frequency Intravascular Ultrasonic Imaging System for Investigation of Vessel Wall Properties," 1992 IEEE Ultrason. Symp. (1992), pp. 1101–1105, there is disclosed a prototype imaging system based on a 42 MHz, 0.7×0.7 mm lead zirconate titanate transducer built into a tip of a 30 cm long hypodermic stainless steel tube. This transducer has an absorptive epoxy backing and a quarter wave polyvinydlene fluoride (PVDF) matching layer. The signal emitted by the transducer is focused by a parabolic aluminum mirror. However, the system only achieves an axial resolution of 55 microns, which is insufficient to detect anatomical structures such as elastic laminae within arterial walls or atherosclerotic plaque which may require axial resolution on the order of 20 to 30 microns or less.

The imaging system of Griffith et al., U.S. Pat. No. 5,115,814, discloses a device for intravascular tissue characterization having a transducer capable of rotating within a catheter via a drive cable. The catheter is advanced within a vessel to be imaged using a previously positioned guide wire, the guide wire being withdrawn after the catheter is positioned. The imaging probe is thereafter inserted into the guide catheter and operated to obtain images of the vessel under investigation. The transducer is excited by circuitry so as to radiate relatively short duration acoustic bursts into the tissue surrounding the probe assembly while the transducer is rotating. The transducer receives the resulting ultrasonic echo signals reflected by the surrounding tissue. Unfortunately, the system of Griffith et al. is also limited in resolution because it is unfocused, operates at 15–30 MHZ, and uses a ceramic transducer. Roth et al., U.S. Pat. No. 5,207,672, discloses another ultrasonic imager that uses miniature transducers mounted within a catheter unit. The device disclosed in Roth et al. uses a pair of miniature transducers, one of which functions as a narrowband ultrasonic transmitter operating at about 7.5 MHz, and a second which functions as an ultrasonic receiver. A single transducer, or an array of transducers, may alternatively be used. A scanning motor is used to rotate the transducers so that image information received from a plurality of angular positions can be received, processed, stored, and displayed. A processor controller provides signals to the transmitting transducer, which generates an acoustic signal in response thereto. The receiving transducer receives reflected acoustic signals, which are converted into signals that are amplified, and digitized. However, the imager disclosed in Roth et al. is not suitable for the detection of elastic laminae within arterial walls or other anatomical features in that it is a narrowband device apparently not capable of operating at the higher frequencies necessary to image tissue characteristics requiring very high axial resolution. Thus, it appears that there are no broad band transducers available which are capable of providing the axial resolution necessary to image certain types of discrete in vivo features.

In manufacturing a broad band transducer using standard microfabrication techniques, the use of inorganic piezoelectric materials such as lead zirconate titanate (PZT) or zinc oxide (ZnO) are disfavored because they are brittle, difficult to deposit, and limited in the total strain that they can achieve. However, polyvinylidene fluoride (PVDF) is an organic piezoelectric material that overcomes some of these problems, and has previously been used in ultrasonic transducers (e.g., Mo et at., "Micromachining for Improvement of Integrated Ultrasonic Transducer Sensitivity," IEEE Trans. on Elec. Dev., Vol. 37, No. 1, Jan., 1990, pp. 134–140). Several advantages of PVDF over the inorganic compounds PZT and ZnO are its lower piezoelectric coefficient and lower thermal and chemical resistance. However, once being extruded and poled to be made piezoelectric, PVDF sheets must be adhered mechanically to the silicon substrate, which is not a standard microfabrication technique. Alternatively, the copolymer of PVDF with trifluorethylene (PVDF-TREE) can be spin-cast from solution directly onto substrates and then poled to be made piezoelectric without requiting extrusion. Suspended piezoelectric membranes using PDVF-TrFE films on silicon wafers have been described by Rashidian et al. in "Integrated Piezoelectric Polymers for Microsensing and Microactuation Applications," DSC-Vol. 32, Micromechanical Sensors, Actuators, and Systems, ASME 1991, ppo 171–179. However, no attempt at modifying such integrated devices for medical imaging applications requiring high resolution has been reported, presumably because of the difficulty in providing an acoustic impedance matched backing for wideband pulse echo imaging. Additionally, no attempts at focusing a wideband acoustic microscope which is integrated into a planar structure have been reported.

The use of a planar-structure focusing lens in a reflection-mode acoustic microscope was proposed in Yamada et al., "Planar-Structure Focusing Lens for Operation at 200 MHz and its Application to the Reflection-Mode Acoustic Microscope," 1986 IEEE Ultrasonic. Syrup. (1986), pp. 745–748. The disclosed configuration requires a thin film ZnO transducer at one end of a 10 mm diameter, 12 mm long fused quartz rod. The opposite end of the rod is etched into a planar lens using a gas plasma created by a microwave electron cyclotron resonance reactive ion etching technique. By this technique, a 200 MHz lens having focal length F=1.5 mm, aperture diameter 3.0 mm and aperture angle 2Θ=90° was prepared. However, the large size of the focusing lens is not readily adaptable to in vivo diagnostic use.

A smaller and thinner lens structure can be made by exciting a thin-plate acoustic transducer only in regions corresponding to the transmissive zones of a Fresnel zone plate (FZP) pattern. A transducer using this technique to focus acoustic waves in water at frequencies near 10 MHz has been reported in Farnow et at., "Acoustic Fresnel Zone Plate Transducers," App. Phys. Letters, Vol. 25, No. 12, Dec. 15, 1994, pp. 681–682. A PZT transducer having one full-face electrode and a zone plate electrode on the other face thereof results in a transducer having an intensity distribution with a half-width of as little as 8.8 mil in the plane of focus. The primary focus is at a distance of 0.67 in. in water. Although this transducer does not require a large quartz focusing lens, the reported focusing dimensions do not lend themselves to intravascular medical imaging applications, and the operating frequency of the transducer is too low to provide the wide bandwidth ultrasound signal needed to provide the axial resolution necessary for certain types of in vivo tissue characterization. A further discussion of the focusing properties of acoustic transducers utilizing FZP electrode patterns has been published in Sleva et al., "Design and construction of a PVDF Fresnel Lens," 1990 IEEE Ultrason. Sympo (1990), pp. 821–826.

The high electrical input impedance associated with the small device dimensions of a transducer required for intravascular imaging suggests that it would be highly advantageous to provide buffer amplifiers and switching circuitry as close as possible to the transducer to achieve adequate signal-to-noise ratios. It would thus be advantageous from a manufacturing standpoint if a wideband transducer suitable for detection of cardiovascular defects and having dimensions appropriate for a catheter could be manufactured and pre-focused using standard microfabrication techniques that permit electronics associated with the transducer to be processed together with the transducer on the same substrate. The device in U.S. Pat. No. 5,041,849 to Quate et al. discloses a fresnel lens manufactured using standard microfabrication techniques. However, this device is designed for high-efficiency, narrow bandwidth applications such as acoustic ink printing.

Thus, the development of a wideband ultrasonic transducer having an integrated Fresnel lens is therefore needed to overcome the disadvantages of pulse echo imaging with presently known transducers.

BRIEF DESCRIPTION OF THE INVENTION

The improved transducer of the present invention comprises a semiconductor base having a void extending through a portion of the semiconductor base from the top surface to the bottom surface. A dielectric layer is disposed on the top surface of the semiconductor base, spanning the void in the semiconductor base. A first conductive electrode layer is disposed thereon. On top of the first conductive electrode layer is a piezoelectric film having a second conducting layer disposed on top of it. Either the first or the second conducting layer, or both, include means for focusing an ultrasonic signal emitted from the piezoelectric layer. The void in the semiconductor base is filled with a material to provide an essentially acoustically matched backing for the transducer. This inventive transducer structure, due to the acoustic impedance of the material filling the void, is able to achieve the wide bandwidths necessary to transmit the wideband signal required by the inventive system. Moreover, because the transducer may be fabricated using standard microfabrication techniques, it is also possible to integrate buffer amplifiers and switching circuitry on the same chip as the transducer.

Focusing may be provided by the conducting layers by patterning a Fresnel zone pattern (FZP) in one or both of the conducting layers. The use of such an integral, planar focusing means eliminates the need for precise machining required for a spherical lens catheter, and yet sufficiently limits the beam width to avoid interference from off-axis structures that would otherwise interfere with the detection of a layered structure in the focused direction.

A piezoelectric polymer of PVDF-TrFE is preferably used for the piezoelectric layer of the integrated transducer, because a layer of this polymer may be applied using techniques compatible with the standard microfabrication techniques presently used with semiconductor substrates such as spin casting. The use of piezoelectric polymers for ultrasound imaging is suggested by their relatively low characteristic acoustic impedances (approximately 4 to 4.5 MRayls), which are closely matched with those of healthy human tissue and water (approximately 1.5 MRayls for both). The close acoustic impedance match provides an efficient transfer of energy from the transducer to the surrounding medium, analogous to transmission line impedance matching.

The same acoustic impedance matching principle is utilized in choosing a material to fill the void in the semiconductor base which is closely match to the piezoelectric polymer. The material chosen for the purposes of illustrating the preferred embodiment of the present invention is an epoxy having an acoustic impedance of approximately 3 to 3.5 MRayls. Consequently, the energy transmitted to the rear of the conductors upon excitation is emitted into the epoxy and absorbed rather than reflected back into the transducer which would result in a ringing affect. As a result, the transducer is capable of transmitting broad band signals which are required to image in vivo structures or features requiting a high resolution in the order of 20–30 microns.

Other objects, features, and advantages of the invention will appear or be made clear and apparent to one skilled in the art from the detailed description below when read in conjunction with the drawings.

DETAILED DESCRIPTION OF THE PREFERRED EMBODIMENT

The preferred embodiment of the present invention is now described with reference to the figures, wherein like numbers represent like parts throughout the figures. While specific techniques for producing etch stop layers, depositing dielectric layers, and etching materials are presented here, for the most part these will be recognized by those skilled in the art as standard microelectronic processing techniques, for which other equivalent techniques may be substituted. Moreover, any low-temperature technique (<80° c.) may be used to deposit the metal conducting layers or layers of any other suitable conductor. It is required only that the conductor deposition method not adversely affect previously processed electronic circuitry on the semiconductor substrate, if any such circuitry exists, and that the deposition method not seriously degrade the PVDF-TrFE piezoelectric film.

Figure 1:
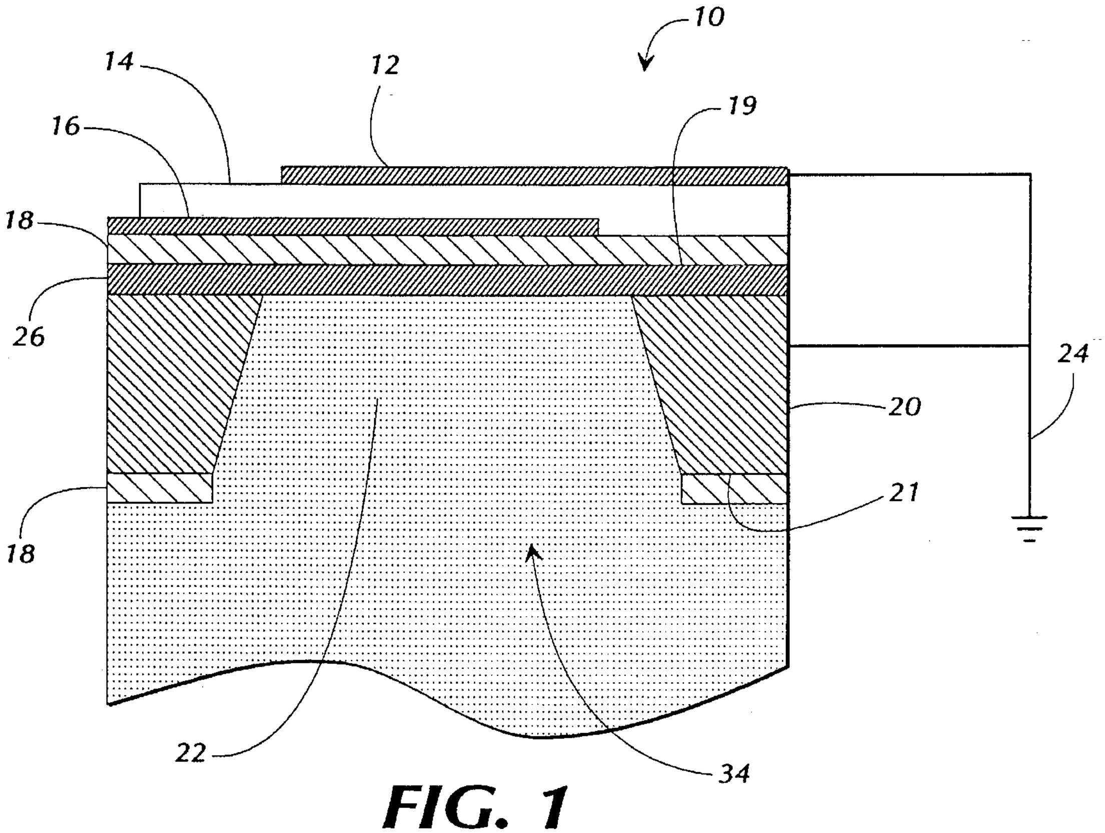
FIG. 1 is a cross-sectional elevation view of an embodiment of a wideband acoustic transducer in accordance with the invention.

An example of a preferred embodiment of an ultrasonic transducer 10 on a semiconductor base in accordance with the invention is depicted in FIG. 1. The illustrated transducer may be fabricated on a base layer 20 of lightly doped (p–) silicon substrate having a top layer 26 of heavily doped (p+) silicon, a polished top side 19, and an unpolished bottom side 21. The p+ silicon layer 26 is preferably formed by diffusing boron into the polished side 19 of the p– silicon base layer 20 to a depth of 5 microns. A dielectric layer 18 is deposited on top of the p+ silicon layer 26 and also on the unpolished side 21. Dielectric layer 18 may be any depositable, insulating dielectric substance such as an oxide or nitride, e.g., silicon dioxide, silicon nitride, or a layered combination of both silicon nitride and silicon dioxide known as a compound dielectric structure. It is preferred that the dielectric layer 18 disposed over the p+ silicon layer 26 be about 4000 Angstroms thick, while the dielectric layer over the bottom side 21 be about 3000 Angstroms thick. Silicon nitride may be deposited using plasma-enhanced chemical vapor deposition (PECVD). A window is etched in the dielectric mask on the unpolished side 21 of the wafer using standard photolithography (photoresist mask) and a reactive ion etch (RIE). The silicon is then etched through the window using an alkaline etch such as potassium hydroxide (KOH). This etchant stops at the p+ silicon layer 26, creating a void 34 and a 5 micron support membrane comprising the unetched p+ layer 26 above void 34. This unetched portion of p+ silicon layer 26 provides mechanical support for the fabrication of the transducer and is removed with a plasma etch when and if it is no longer needed.

Figure 2A:
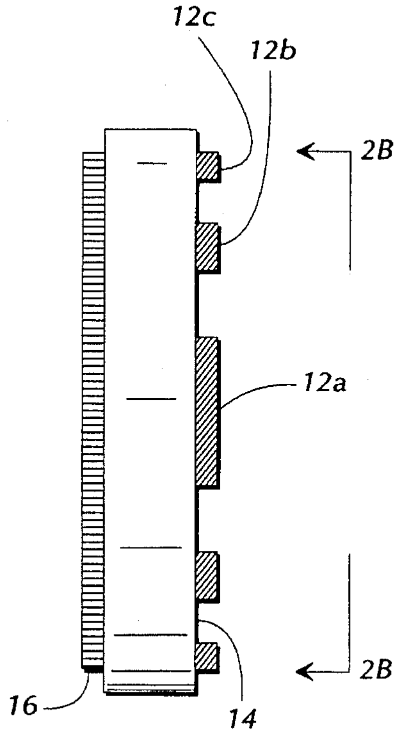
FIG. 2A is a cross-sectional elevation view of a portion of the transducer in FIG. 1 showing the conductive and piezoelectric layer.
Figure 2B:
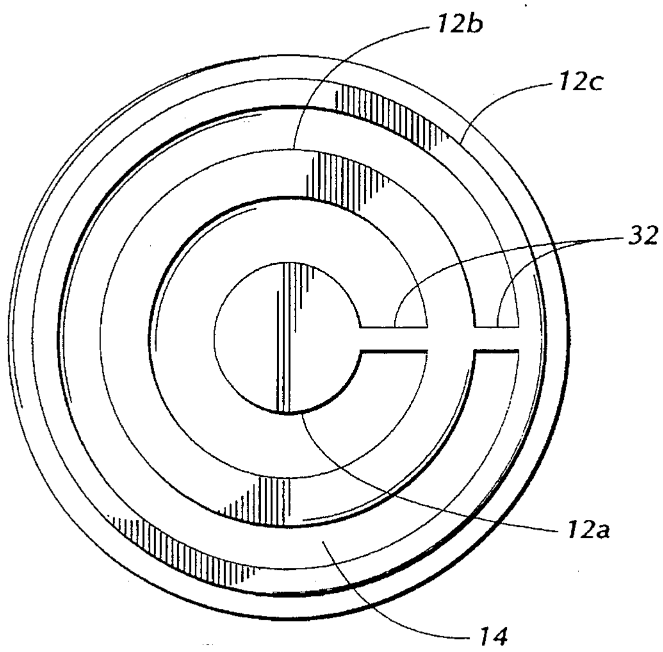
FIG. 2B is a plane view of the transducer of FIG. 2A.

Metal is then deposited for the first conductive electrode 16 on top of the dielectric layer 18 using an electron beam (E-beam) or a thermal evaporator. The first conductive electrode 16 is patterned using standard photolithography, and unwanted metal is etched away using an enchant appropriate for the conductor used. Next, a solution, such as PVDF-TrFE, is spin-cast on top of the first conductive electrode 16 and then heat-cured to create a uniform piezoelectric film 14. Alignment of the electrode patterns is made somewhat more difficult because the etch process requires that the entire upper surface of film 14 be covered by the metal used to produce a second conductive electrode 12 before lithography is done, which, unfortunately, also covers any alignment marks in the first conductive electrode 16 pattern. However, a removable fill (which may be as simple as a piece of cellophane adhesive tape) may be adhered to the piezoelectric film 14 above alignment marks in the first conductive electrode 16. Metal for the second conductive electrode 12 is then deposited on top of the film 14 using an E-beam or a thermal evaporator. The tape may then be removed to expose the alignment marks, which are then visible through film 14. The second conductive electrode 12 is then patterned using standard photolithography, and etched away using etchants appropriate for the metals used. To achieve the desired focusing characteristics, it is important that at least one of the first or second conductive electrodes 12, 16 define a Fresnel zone plate pattern above void 34, as shown in FIGS. 2A and 2B. The portion of the p+ silicon layer 26 above void 34 is then removed by etching with a reactive ion etch, such as a 80% $CF_4$/20% $O_2$ plasma, to expose the dielectric layer 18, because the p+ silicon layer 26 would otherwise act as a capacitor with first conductive electrode 16, thereby limiting the sensitivity of the transducer.

The film 14 may be poled (polarized) in at least two preferred ways. The first is using a corona discharge method immediately after film 14 is heat-cured. The other is to use a DC thermal poling process after the p+ silicon layer 26 is etched away above void 34. The latter process may be accomplished by connecting conductive electrodes 12 and 16 to a variable 10 kV supply and raising the temperature of the film 14 to about 80° C. A sufficient voltage is then applied to the conductive electrodes 12, 16 across the film to produce an electric field of at least 100 v/micron in the film. The temperature is then reduced with the field in place to fix the polarization, yielding a film 14 that exhibits substantial piezoelectric properties.

After the conductive electrodes 12, 16 have been deposited and patterned, and after the PVDF-TrFE film 14 has been poled, a thick layer 22 of epoxy or mixture of epoxy and metal dust is used to fill in void 34 in silicon base layer 20. Additional epoxy may be added after the initial filling of epoxy has cured, until the layer of epoxy exceeds a thickness of preferably more than 100 acoustic wavelengths of the center frequency. A portion of the first conductive electrode 16 that is not covered by the second conductive electrode 12 is used as a bonding tab, which may be exposed to accommodate an electrical connection by dissolving in acetone a small area of film 14 covering the portion of conductive electrode 16 to be exposed. Contact between the bonding tabs and wires may be made using conductive silver paint or conductive epoxy. Either the first conductive electrode 16 or the second conductive electrode 12 may be connected to a circuit ground 24.

Second conductive electrode 12 preferably comprises deposited gold, for resistance to corrosion, or a protective dielectric layer may be deposited over second conductive electrode 12 to allow a less noble metal to be used. First conductive electrode 16 may comprise a deposit of less expensive aluminum because it is protected from air, water and blood by film 14 deposited on top of it.

As described hereinbefore, to achieve the required focusing without external focusing means, either the first or the second conductive electrodes 12, 16, or both, must be deposited in a Fresnel zone pattern (FZP). If one of the conductive electrodes 12, 16 is deposited in an FZP, then the other may be deposited in a solid pattern. An illustration (not to scale) of a second conductive electrode 12 comprising Fresnel zones 12*a*, 12*b*, and 12*c* is shown in FIGS. 2A and 2B, which represent a side and top view, respectively, of the active portion of the structure shown in FIG. 1. Interzone electrical connections 32, shown in FIG. 2B, are necessary to provide continuity between the bullseye-like tings 12*a*, 12*b*, and 12*c*. First conductive electrode 16 is deposited in a solid, preferably circular pattern on the other side of the piezoelectric material comprising film 14 directly opposite the second conductive electrode 12. The circumference of first conductive electrode 16 is at least as great as the outer Fresnel zone 12*c*. Of course, it is possible to have a lesser or greater number of Fresnel zones than is shown in FIGS. 2A and 2B, but three zones results in a reasonable f-number (ratio of focal length to lens diameter) of slightly greater than 1 at a 50 MHz center frequency and a reasonable outer diameter for the outermost zone (less than 1 mm). The resulting transducer has dimensions suitable for fitting in a 5 French catheter. In any event, no advantage accrues to using more than about 7 zones, since such a Fresnel lens approximates the focusing performance of a spherical lens with the same f-number fairy closely.

The zone radii that define the pattern of a Fresnel zone plate are give by equation (1) below:

$$r_m = \left[ \frac{m\lambda}{2} + \left( Z_o + \frac{m\lambda}{8} \right) \right]^{1/2} ;\ m = 1,3,5, \ldots \quad (1)$$

where $Z_o$ is the focal length, $r_m$ is the zone radii as shown in FIG. 2B, and λ is the acoustic wavelength in the medium into which the device is radiating. The zone plate electrode pattern is an amplitude grating since acoustic signals are excited only by those zones which are covered by the electrode. Ideally, the signals excited by each zone are of equal amplitude and are in phase.

Significant impedance mismatch between the transducer material and backing material can result in a narrow band device which "rings" when excited by a short duration electrical signal. Thus, the acoustic signal is significantly longer in duration than the electrical signal, limiting axial resolution. The present invention solves this ringing problem by providing a matched acoustical backing layer 22 filling void 34. An epoxy or metal loaded epoxy having an acoustic impedance matched with that of the piezoelectric film 14 provides such an acoustical backing layer 22 so as to minimize or eliminate reflections at the rear of the ultrasonic transducer 10, and thereby acoustically increasing the bandwidth and decreasing the ringing of the transducer. An epoxy found to be suitable for use with the inventive transducer structure, which has an acoustic impedance of approximately 3.0–3.5 MRayls and a viscosity low enough to enable it to be poured into the void 34 and cured essentially free up air bubbles, is Everfix® two-part epoxy, model 643, made by Fibre Glass-Evercoat Co., Inc. The epoxy can be used as it is supplied, or it may be mixed with a metal powder such as tungsten to raise the acoustic impedance slightly, as the acoustic impedance of the model 643 epoxy is slightly lower than PVDF-TrFE. However, mixing the epoxy with a metal powder is not preferred because the mixture becomes too viscous, and the acoustic impedance match achieved using the epoxy by itself is sufficient to provide adequate bandwidth. The thickness of the epoxy layer is preferably many (approximately 100 times or more) acoustic wavelengths, so that all of the acoustic energy radiated into the epoxy is absorbed. Additionally, the impedance of a piezoelectric film 14 comprising PVD-TrFE is close enough to that of water and human tissue so that reflections at the front of the ultrasonic transducer 10 are minimized.

The back filling technique described above avoids conventional bonding of the transducer to the matched backing, which would otherwise require that the backing be polished carefully to avoid distortions in the film. Avoiding conventional bonding is important because such mechanical bonding would be difficult in view of the fragile nature of the silicon substrate and the membrane.

A preferred method for fabricating the conductive layers is now described in more detail. An approximately 1000 Angstrom aluminum (A1) layer is deposited on top of the p+ silicon layer 26 using electron-beam evaporation so as to form first conductive electrode 16. Photoresist is spin-cast over the AI electrode 16 and is patterned using photolithography to create a Fresnel zone plate (FZP) electrode pattern over the p+ silicon layer 26. The FZP pattern is used to focus the ultrasound while maintaining a planar structure. The A1 electrode 16 is then etched using a PAN solution (16:1:1:2 phosphoric acid: acetic acid: nitric acid: water) and the unexposed photoresist is removed. The PVDF-TrFE solution is then spin-cast onto the wafer to form film 14 and a gold (Au) layer is deposited to form second conductive electrode 12. Because the upper electrode will normally be protected with a protective layer 58 (shown in FIG. 3), it is not necessary to use Au for second conductive electrode 12. Any metal may be used as long as it is kept thin enough to be acoustically transparent. However, it is critical that the second conductive electrode 12 material have good adhesion with the PVDF-TrFE film 14. Therefore, if Au is used for the second conductive electrode 12, a layer of chrome or titanium (not shown) must be used as an adhesion layer between the Au second conductive electrode 12 and the film 14o If A1 is used for the second conductive electrode 12, the PAN enchant solution described above may be used.

The portion of the layer 18 of dielectric remaining over the unpolished side 21 of silicon base layer 20 may be removed using a plasma or reactive ion etch, but it is not necessary to do so.

The preferred embodiment of transducer 10 may be part of an integrated circuit that is formed on the same base layer 20. However, PVDF-TrFE is soluble in many of the solvents typically used in standard microelectronics processing techniques, so no solvents are used in processing (except to expose contacts for conductive film 16) once the PVDF-TrFE layer 14 has been spin-cast. Instead, solvents are avoided by using an etch process rather than the more conventional liftoff. In addition, once the material has been poled, it cannot be exposed to temperatures greater than about 80° C. or the material may become unpolled.

Figure 3:
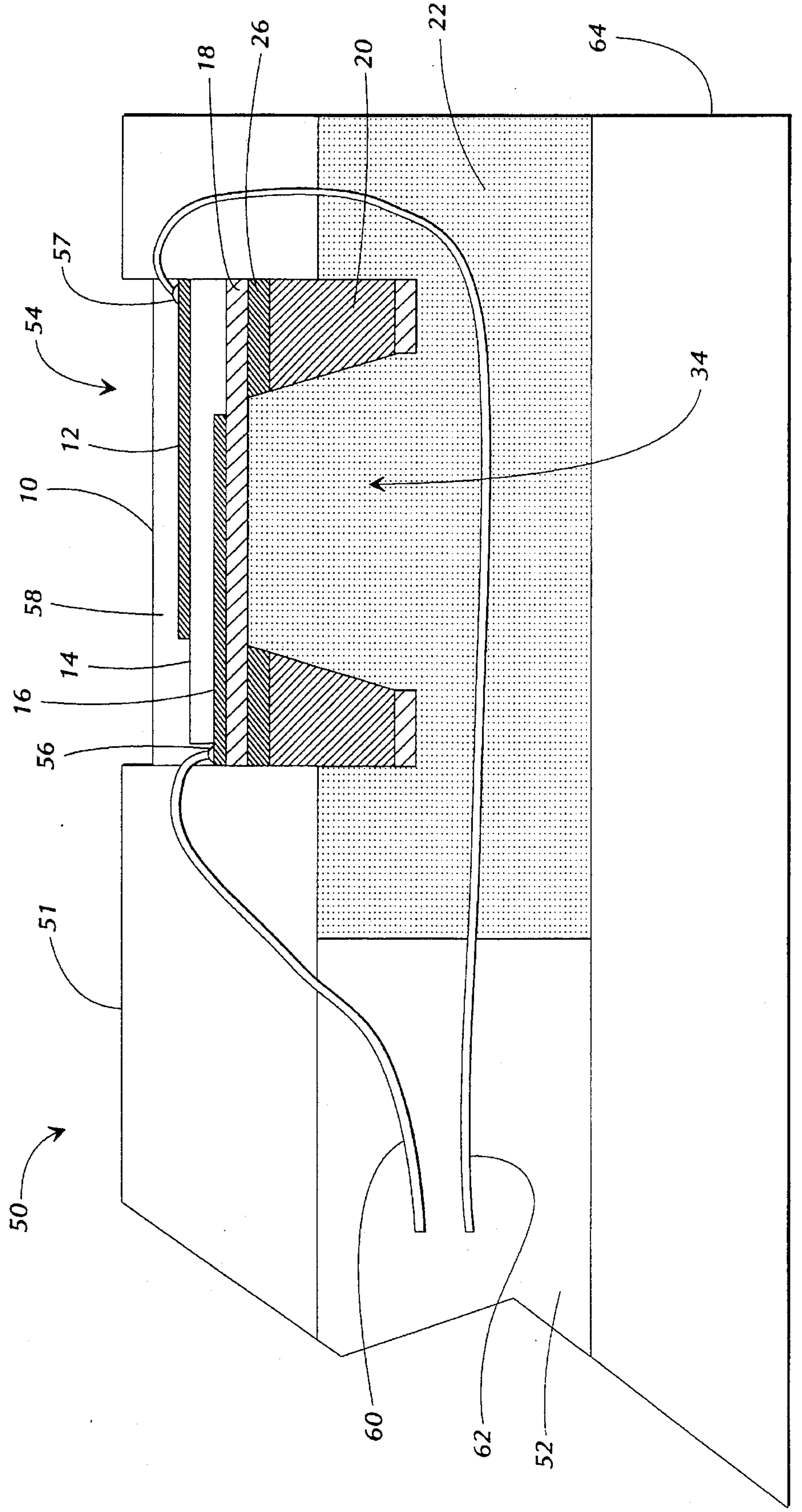
FIG. 3 is a cross-sectional view of a catheter tip incorporating the transducer of FIG. 1 in accordance with the present invention.

FIG. 3 is a cross-sectional view of a catheter tip incorporating a transducer 10 in accordance with the invention. Transducer 10 is affixed within a recess 54 providing a tight fit for transducer 10 near a tip 64 of hollow catheter 50. Recess 54 communicates with bore 52 in catheter 50. Bore 52 is filled with epoxy 22 in the area of communication with recess 54, so that, when transducer 10 is pressed into recess 54, epoxy 22, which provides an acoustically matched backing, fills void 34 in transducer substrate base layer 20. Transducer 10 should preferably be pressed into recess 54 until protective layer 58 if flush with or below the level of the surrounding outer wall 51 of catheter 50. Bore 52 may be closed off in the vicinity of tip 64 with epoxy 22, or catheter 50 may be provided with an integral closed end. Electrical contact is made with the conductive electrodes 12, 16 of transducer 10 via wires 60 and 62, which may be connected to pads 56 and 57, respectively, on transducer 10. Wires 60 and 62 are threaded by any suitable path into bore 52, and may be connected to any suitable two-conductor cable, such as a microminiature coaxial cable (not shown). One conductive electrode of transducer 10 may be grounded or a balanced drive signal without a ground may be supplied, as is contemplated in FIG. 3.

It will be recognized that the small size of the transducer makes possible various medical uses that may not previously have been practical. For example, in accordance with the present invention, a chip containing an ultrasonic transducer and its associated electronics is sufficiently small to allow implantation in the body of a patient, along with a suitable power supply (e.g., such as those presently used in pacemakers). In normal operation, the implanted device awaits a recognizable "wakeup" signal. The "wake-up" signal may be supplied by any suitable means from outside the body, such as by a magnetic, electromagnetic, or acoustical signal. The electrical circuitry can then cause the transducer to insonify tissue and cause a signal representative of the echo signal received by the transducer to be transmitted (e.g., by radio) outside the body and then returned to inactive mode, avoiding the need for the patient to undergo surgery each time a tissue characterization is required.

Figure 4:
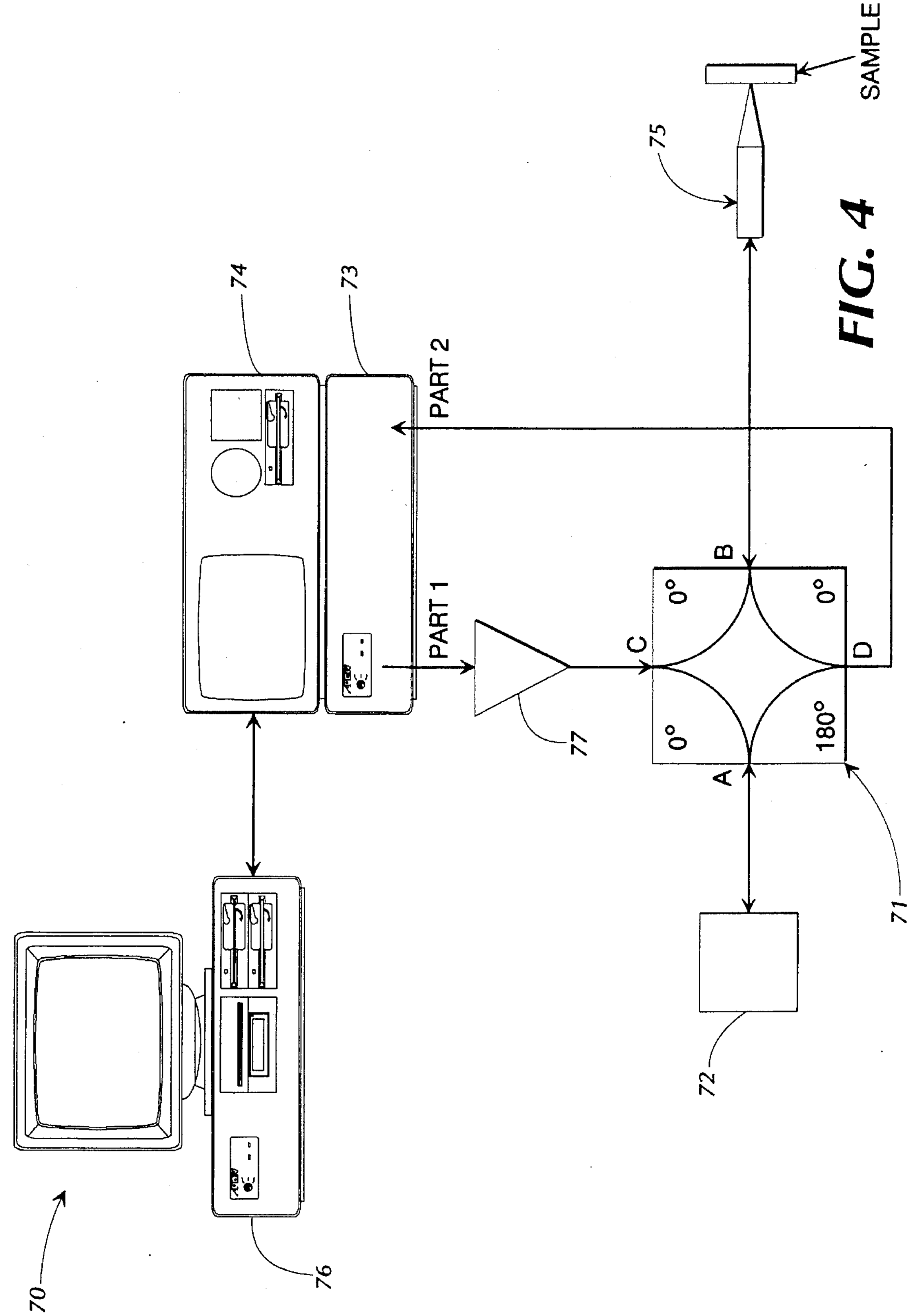
FIG. 4 is a diagram of a diagnostic system incorporating the wideband ultrasonic transducer of the invention.

The inventive broad band ultrasonic transducer 10 is especially suited for characterizing features or structures requiring very high resolution. A novel tissue characterization or non-destructive evaluation (NDE) system 70 capable of achieving high axial resolution through broad band signaling has been developed using transducer 10. System 70, as shown in FIG. 4, comprises a network analyzer 74, such as a Hewlett Packard Model 875313 selected for a Fourier transform, connected to a S-parameter test set 73, such as Hewlett Packard Model 87046A. Connected to port 1 of the test set 73 is the input to a linear rf amplifier 77, the output of which connects to one port of a 180° hybrid junction 71, such as a Macom Model H-9. Junction 71 has three other ports connected to a mock circuit 72, catheter 75 having broad band transducer 10 integrated therein, and port 2 of test set 73.

In operation, the signal out of port 1 of the test set 73 is amplified 26 dBm by amplifier 77, then input to port C of junction 71. The signal at port C of junction 71 is applied to both mock circuit 72 at port A and transducer 10 at port B. Ideally, mock circuit 72 has the same input impedance as transducer 10 so that the initial reflected signals at ports A and B are equal. Thus, the 180° phase shift introduced between ports A and B by junction 71 causes the signals to cancel each other at port D of junction 71.

The initial reflected signal due to the high electrical input impedance of transducer 10 is typically much greater than the signal due to the acoustic echo. Further, the initial reflected signal may arrive several microseconds to several tens of microseconds before the acoustic echo. Consequently, if the initial reflected signal from transducer 10 is not canceled by the initial reflected signal from mock circuit 72, the reflected signal may overload the input port of network analyzer 74. This would result in an automatic reduction in the output power which limits the maximum output power and thus the dynamic range of system 70.

However, because the initial reflected signal is canceled, the response signal at port B of junction 71 due to the acoustic echo received by transducer 10 appears at port D of junction 71, and thus port 2 of test set 73. Network analyzer 74 then measures the network parameter $S_{21}$, the resulting signal of which can be sent to a computer 76 for storage, analysis, or display.

It should also be recognized that the present invention is not limited to the insonification and characterization of tissue, but may be used to insonify and characterize other objects of interest. In addition, it will be noted that diagnostic systems using two (or more) transducers are possible, including embodiments with separate transmitting and receiving transducers on the same substrate and mounted in a catheter.

Moreover, it will be understood that the invention is not restricted to the particular embodiments described herein, and that many modifications may be made to such embodiments by one skilled in the art without departing from the spirit of the invention or the scope of the claims.

We claim:

1. A wide bandwidth ultrasonic transducer capable of both transmitting and receiving signals, comprising:

a semiconductor base having a first layer which is heavily doped, a second layer which is lightly doped, and a void formed therein;

a dielectric layer disposed on said first layer of said semiconductor base and spanning said void in said semiconductor base such that said dielectric layer has a first surface in contact with said first layer of said semiconductor base;

a first conductive electrode disposed on a second surface of said dielectric layer and having a first surface in contact with said second surface of said dielectric layer, said conducting electrode having a second surface opposite said first surface of said first conductive layer;

a piezoelectric film disposed on said second surface of said first conductive electrode layer and having a first surface in contact with said second surface of said first conductive electrode, said piezoelectric film having a second surface opposite said first surface;

a second conductive electrode disposed on said second surface of said piezoelectric film and having a first surface in contact with said second surface of said piezoelectric film, said second conductive layer having a second surface opposite said first surface;

a Fresnel zone plate pattern in at least one of said first conductive electrode and said second conductive electrode for focusing ultrasound waves emitting from said transducer; and backing means disposed in said void, said backing means having an acoustic impedance substantially matched to said piezoelectric layer.

2. The wide bandwidth ultrasonic transducer of claim 1, wherein said semiconductor base comprises silicon.

3. The wide bandwidth ultrasonic transducer of claim 1, wherein said piezoelectric film comprises PVDF-TrFE.

4. The wide bandwidth ultrasonic transducer of claim 1, wherein said semiconductor base comprises integrated electronic circuitry associated with said wideband ultrasonic transducer.

5. The wide bandwidth transducer of claim 1, wherein said void in said semiconductor base extends through said first layer of said semiconductor base.

6. The wide bandwidth transducer of claim 1, wherein said void in said semiconductor base extends through second layer of said semiconductor base.

7. The wide bandwidth transducer of claim 1, wherein said backing means absorbs substantially all the energy transmitted toward said semiconductor base when said transducer is electrically excited.

8. The wide bandwidth transducer of claim 1, wherein said backing means comprises a filling disposed in said void, said filling having an acoustic impedance between 1.0 to 4.5 MRayls.

9. The wide bandwidth transducer of claim 1, wherein said backing means is an epoxy.

10. The wide bandwidth transducer of claim 1, wherein said backing means is a metal loaded epoxy.

11. A wide bandwidth ultrasonic transducer comprising:

a piezoelectric layer having a first and second surface;

a first conductive electrode attached to said piezoelectric layer, said first conductive electrode having a first surface in contact with said first surface of said piezoelectric layer, said first conductive layer having a second surface opposite said first surface;

a second conductive electrode attached to said second surface of said piezoelectric layer;

focusing means in at least one of said first conductive electrode and said second conductive electrode;

a dielectric layer attached to said first conductive electrode, said dielectric layer having a first surface in contact with said second surface of said first conductive electrode, said dielectric layer having a second surface opposite said first surface;

a semiconductive base layer attached to said dielectric layer, said semiconductor base layer having a first surface in contact with said second surface of said dielectric layer, said semiconductor base layer having a second surface opposite said first surface;

said semiconductor base layer having a void in said second surface, said void aligned with a portion of said piezoelectric layer in contact with said first conductive layer on said first surface of said piezoelectric layer and said second conductive electrode on said second surface as a piezoelectric layer; and said void filled with a backing means having an acoustic impedance substantially matched to said piezoelectric layer.

* * * * *